United States Patent
Wasse et al.

(10) Patent No.: US 9,724,412 B2
(45) Date of Patent: Aug. 8, 2017

(54) CHYMASE COMPOSITIONS, ANTIBODIES, DIAGNOSTICS, AND THERAPEUTIC METHODS RELATED THERETO

(75) Inventors: Haimanot Wasse, Atlanta, GA (US); Ahsan Husain, Atlanta, GA (US); Nawazish Ali Naqvi, Liburn, GA (US)

(73) Assignee: Emory University, Atlanta, GA (US)

( * ) Notice: Subject to any disclaimer, the term of this patent is extended or adjusted under 35 U.S.C. 154(b) by 185 days.

(21) Appl. No.: 14/127,206

(22) PCT Filed: Jul. 11, 2012

(86) PCT No.: PCT/US2012/046134
§ 371 (c)(1),
(2), (4) Date: Apr. 9, 2014

(87) PCT Pub. No.: WO2013/009793
PCT Pub. Date: Jan. 17, 2013

(65) Prior Publication Data
US 2014/0220024 A1 Aug. 7, 2014

Related U.S. Application Data

(60) Provisional application No. 61/506,854, filed on Jul. 12, 2011.

(51) Int. Cl.
| | | |
|---|---|---|
| G01N 33/573 | (2006.01) | |
| A61K 39/395 | (2006.01) | |
| A61K 45/06 | (2006.01) | |
| C07K 16/40 | (2006.01) | |
| C12N 9/64 | (2006.01) | |

(52) U.S. Cl.
CPC .......... *A61K 39/3955* (2013.01); *A61K 45/06* (2013.01); *C07K 16/40* (2013.01); *C12N 9/6483* (2013.01); *G01N 33/573* (2013.01); *C07K 2317/34* (2013.01); *G01N 2333/96433* (2013.01); *G01N 2333/96483* (2013.01); *G01N 2800/347* (2013.01)

(58) Field of Classification Search
None
See application file for complete search history.

(56) References Cited

U.S. PATENT DOCUMENTS

2003/0229007 A1* 12/2003 Levi et al. ................... 514/2

FOREIGN PATENT DOCUMENTS

| JP | 2003-235556 A | | 8/2003 |
|---|---|---|---|
| JP | 2003235556 A | * | 8/2003 |

OTHER PUBLICATIONS

Waiker et al (J Am Soc Nephrol. Jan. 2012; 23(1): 13-21).*
Jin et al (J Am Soc Nephrol. Apr. 2005;16(4):1024-34. Epub Mar. 2, 2005).*
Jin et al. "Effect of chymase inhibition on the arteriovenous fistula stenosis in dogs" J Am Soc Nephrol., 2005; 16(4): 1024-1034.
Lynch et al. "Achieving the Goal of the Fistula First Breakthrough Initiative for Prevalent Maintenance Hemodialysis Patients" Am J Kidney Dis., 2011; 57(1): 78-89.
Sun et al. "Critical Role of Mast Cell Chymase in Mouse Abdominal Aortic Aneurysm Formation" Circulation, 2009; 120(11): 973-982.
Takai et al. "A novel chymase inhibitor, 2-(5-formylamino-6-oxo-2-phenyl-1,6-dihydropyrimidine-1-yl)-N-[[,4-dioxo-1-phenyl-7-(2-pyridyloxy)]2-heptyl]acetamide (NK3201), suppressed intimal hyperplasia after balloon injury" J Pharmacol Exp Ther., 2003; 304(2): 841-844.
Waikar et al. "Imperfect Gold Standards for Kidney Injury Biomarker Evaluation" J Am Soc Nephrol., Jan. 2012; 23(1): 13-21.
Wang et al. "Elevated Plasma Chymotrypsin-like Protease (Chymase) Activity in Women with Preeclampsia" Hypertension in Pregnancy, 2010; 29: 253-261.
Wasse et al. "Impact of Mast Cell Chymase on Renal Disease Progression" Curr Hypertens Rev., 2012; 8(1): 15-23.
Wasse et al. "Increased Plasma Chymase Concentration and Mast Cell Chymase Expression in Venous Neointimal Lesions of Patients with CKD and ESRD" Semin Dial, 2011; 24(6): 688-693.
Wei et al. "Mast cell chymase limits the cardiac efficacy of Ang I-converting enzyme inhibitor therapy in rodents" J Clin Invest., 2010; 120(4): 1229-1239.

* cited by examiner

Primary Examiner — Brian J Gangle
Assistant Examiner — Andrea McCollum
(74) Attorney, Agent, or Firm — Emory Patent Group

(57) ABSTRACT

The disclosure relates to chymase, antibodies to chymase, and diagnostic and therapeutic methods relates thereto. It has been discovered that above certain circulating levels of chymase, a patient has a high likelihood of arteriovenous fistula nonmaturation. Compositions and methods of detecting and measuring chymase levels are disclosure herein. In certain embodiments, the disclosure relates to methods of determining the effectiveness of creating an arteriovenous fistula in a subject diagnosed with chronic kidney disease.

3 Claims, 3 Drawing Sheets

SEQUENCE LISTING

```
<160> NUMBER OF SEQ ID NOS: 3

<210> SEQ ID NO 1
<211> LENGTH: 7
<212> TYPE: PRT
<213> ORGANISM: Homo sapiens

<400> SEQUENCE: 1

Pro Ser Lys Phe Cys Gly Gly
1               5

<210> SEQ ID NO 2
<211> LENGTH: 14
<212> TYPE: PRT
<213> ORGANISM: Homo sapiens

<400> SEQUENCE: 2

Glu Ile Val Thr Ser Asn Gly Pro Ser Lys Phe Cys Gly Gly
1               5                   10

<210> SEQ ID NO 3
<211> LENGTH: 15
<212> TYPE: PRT
<213> ORGANISM: Homo sapiens

<400> SEQUENCE: 3

Met Ala Tyr Leu Glu Ile Val Thr Ser Asn Gly Pro Ser Lys Phe
1               5                   10                  15
```

CHYMASE COMPOSITIONS, ANTIBODIES, DIAGNOSTICS, AND THERAPEUTIC METHODS RELATED THERETO

CROSS REFERENCE TO RELATED APPLICATIONS

This application is the National Stage of International Application No. PCT/US2012/046134 filed Jul. 11, 2012, which claims the benefit of priority to U.S. Provisional Application 61/506,854 filed Jul. 12, 2011. The entirety of each of these applications is hereby incorporated by reference for all purposes.

STATEMENT REGARDING FEDERALLY FUNDED RESEARCH

This invention was made with government support under Grants DK065634 and RR025008 both awarded by the National Institutes of Health. The Government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 11053_US_ST25.txt. The text file is 1 KB, was created on Dec. 18, 2013, and is being submitted electronically via EFS-Web.

BACKGROUND

Dialysis is primarily used to provide an artificial replacement for lost kidney function in patients with kidney failure. Patients have different dialysis options. The most common type of dialysis in the United States is hemodialysis. Vascular access, which provides repeated, reliable access to the bloodstream, is required for hemodialysis. The optimal form of hemodialysis vascular access is the arteriovenous fistula (AVF), a conduit surgically created in the arm connecting an artery and a vein, which takes several weeks (up to 12) to properly mature for hemodialysis. Unfortunately, up to 60% of AVF fail to mature properly to sustain chronic hemodialysis.

The primary contributor to AVF nonmaturation is intimal hyperplasia (IH). The tunica intima (intima) is an inner layer of cells in an artery or vein. Intimal hyperplasia (IH) refers to an increase in number or size of cells in the intima resulting in the gross enlargement and potential closing of the artery and/or vein. IH in dialysis arteriovenous (AV) access is accelerated and can result in vessel narrowing leading to reduced AV access blood flow or thrombosis. Consequently, end-stage renal disease (ESRD) patients may require an access intervention every 3-6 months to reestablish and maintain patency and, over time, can exhaust sites for all AV access options in the upper extremities. Currently, there is no effective therapy to treat IH in ESRD patients. An individual patient's susceptibility to IH varies, therefore the ability to predict whether a patient is at greater risk of AVF nonmaturation with consequent increased central venous catheter time as a bridge to AVF maturation, or multiple AV access surgeries, would be beneficial to provide patient's options, such as peritoneal dialysis or AV graft use.

Angiotensin II contributes to IH. Interruption of the renin-angiotensin system with ACE inhibition has been investigated, but does not attenuate IH in humans. Chymase is an ACE-independent angiotensin II-forming enzyme present in blood vessels and contained in the secretory granules of mast cells. With inflammatory stimulus, chymase is released into the vascular interstitium and forms Angiotensin II independent of ACE. Chymase inhibition in animal models is shown to effectively attenuate IH.

SUMMARY

The disclosure relates to chymase, antibodies to chymase, and diagnostic and therapeutic methods related thereto. It has been discovered that above certain circulating levels of chymase, a patient has a high likelihood of AV fistula nonmaturation. After the creation of an arteriovenous fistula (AVF) flow increase and venous dilatation are important to obtain a functioning vascular access (VA) for hemodialysis treatment. Venous dilatation facilitates repetitive cannulations with large calibre needles, while the significant flow rates in the VA enable adequate extra-corporeal perfusion of the dialyzer for the effective hemodialysis treatment. The term "maturation" refers to sufficient venous dilatation and the flow rate increase for effective hemodialysis treatments. The term, "nonmaturation" refers to inadequate increase in blood flow rate that renders VA unsuitable for hemodialysis treatment. For example, within certain embodiments of the disclosure, non-maturation refers to flow through the AVF below 25, 50, 100, 200, 300, 400, or 500 ml/min, and/or a diameter of the AVF of less than 1, 2, 3, 4, or 5 mm.

Compositions and methods of detecting and measuring chymase levels are disclosed herein. In certain embodiments, the disclosure relates to methods of determining the effectiveness of creating an AVF in a subject diagnosed with lowered kidney function or late-stage chronic kidney disease preparing for chronic hemodialysis, comprising a) assaying a sample for a plasma chymase level, wherein the sample is obtained from a subject diagnosed with chronic kidney disease; and b) correlating an elevated level of plasma chymase with a high likelihood of AVF nonmaturation. In certain embodiments, the assaying measurement of the plasma chymase level is recorded, e.g., by electronic memory in a computer. Typically, the method further comprises the step of c) reporting the plasma chymase level to the subject or a medical professional or representative thereof. Typically, an elevated level of plasma chymase refers to chymase with greater than about 150, 175, 200, or 210 ng/mL of sample. In certain embodiments, it is contemplated that the subject his diagnosed with chronic kidney disease or has lowered kidney function because the subject has a creatinine level greater than 1.5 mg/dL or a blood urea nitrogen greater than 20 mg/dL or a glomerular filtration rate of less than 30 or less than 15 mL/min/m$^2$ or is diagnosed to be within 6 months of anticipated dialysis initiation.

In certain embodiments, the assay comprises measuring the plasma chymase level with a chymase antibody that has an epitope comprising a PSKFCGG (SEQ ID: NO 1) amino acid sequence.

In certain embodiments, the disclosure relates to an antibody produced by exposing an animal to a polypeptide consisting essentially of EIVTSNGPSKFCGG (SEQ ID NO: 2), i.e., antibody with an epitope comprising PSKFCGG (SEQ ID NO: 1).

In certain embodiments, the disclosure relates to methods of treating or preventing chronic kidney disease comprising administering a therapeutically effective amount of a chymase inhibitor to a subject diagnosed with, at risk of, or exhibiting symptoms of chronic kidney disease. Typically, the chymase inhibitor is an antibody with an epitope to PSKFCGG (SEQ ID NO: 1). In some embodiments, it is contemplated that the subject received a kidney transplant and that the chymase inhibitor is administered in combination with an ACE (angiotensin-converting enzyme) inhibitor.

DETAILED DISCUSSION

Figure 1:
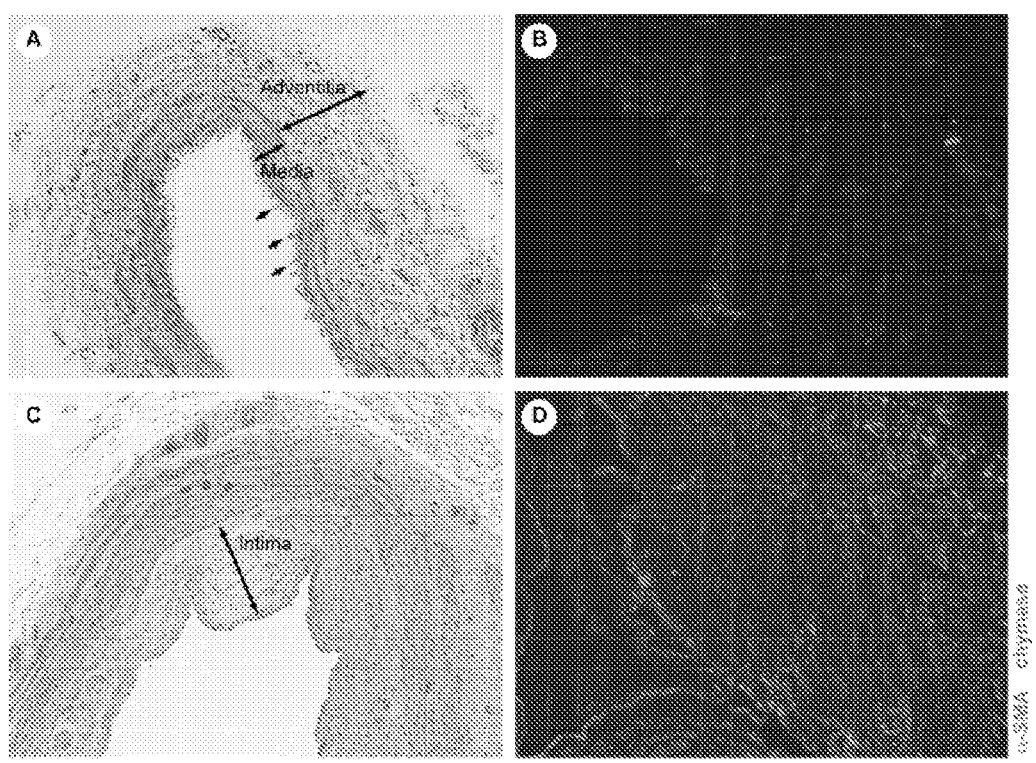
FIG. 1: Non-CKD vein (a, b) with no intimal hyperplasia and minimal chymase activity (green); CKD vein with intimal hyperplasia (c) and abundant chymase (d), co-localized with α-smooth muscle actin (α-SMA).

Chymase is suspected of playing a causative role in the formation of venous IH via stimulation of two primary contributors to IH formation: angiotensin II (Ang II) and transforming growth-factor beta 1 (TGF-β1). Chymase causes Ang II formation, which has been shown to increase the expression of pro-TGF-β and MMP-9. In addition to this indirect effect, chymase also converts the latent form of TGF-β to its active form. These direct and indirect effects of chymase may contribute to IH and fibrosis. The role of chymase in IH formation is supported by the ability of chymase inhibition to attenuate intimal proliferation in canine models of balloon injury, vein grafting, and AV fistula (AVF) creation and AV graft (AVG) insertion.

Uremia is a state of chronic inflammation and oxidative stress. Chymase is believed to play a role in venous IH formation and is highly expressed in the veins of CKD and ESRD patients with IH. Data suggest that mast cell chymase expression may be reflected by an elevated plasma chymase concentration.

Increased Plasma Chymase Concentration and Mast Cell Chymase Expression in Venous Neointimal Lesions of CKD and ESRD Patients Progressive IH restricts AVF blood flow, preventing adequate dialysis and increasing the likelihood of AVF thrombosis. Important contributors to IH development such as chymase are present in veins of CKD and ESRD patients. Plasma chymase is increased as much as a 33-fold in CKD patients. The finding that chymase inhibition attenuates IH in animal models, and findings herein that chymase levels are elevated in venous IH lesions of CKD and ESRD patients suggest that chymase inhibition may be useful therapeutically. It also points to the utility of using plasma chymase as a biomarker to predict AVF nonmaturation.

Studies of mast cell chymase suggest that it is localized to the adventitial layer of blood vessels and that chymase inhibition limits IH development in animal models of vascular injury. In CKD patients it was found that chymase expression is diffuse, with greater chymase immunoreactivity in the vessel intima and media. TGF-β is a well-recognized promoter of VSMC proliferation, and induces fibrosis and ECM production in blood vessels. Studies herein suggest that TGF-β co-localizes with chymase in the veins of subjects with IH, and is most prominent in the intima and media layers of blood vessels. Although it is not intended that embodiments, of the disclosure be limited by any particular mechanism, one possibility for this co-localization is that chymase increases the expression of TGF-β indirectly via promotion of Ang II formation and directly by activating pro-TGF-β1. Another possibility for the chymase/TGF-β/IL-6 co-localization in these diseased vessels could be the finding that mast cells store and release all of these mediators into the vascular interstitium. Chymase and TGF-β in vessels with IH, in addition to IL-6, indicate an inflammatory state and suggest their involvement in IH progression.

Studies herein suggest that plasma chymase levels were increased in CKD patients between 4 and 33-fold. Interestingly, chymase distribution was bimodal, yet there were no significant differences in co-morbidities between the groups except BMI. Circulating chymase levels may be a predictor of extant intimal hyperplasia in patients with CKD. Studies herein suggest significantly greater plasma chymase levels in CKD patients than previous studies on subjects with mastocytosis and aortic aneurysm.

Although there are several endogenous inhibitors of chymase, such as alpha-1 antitrypsin, circulating chymase exists in a protected state in complex with alpha-2 macroglobulin such that it is capable of converting angiotensin I to angiotensin II in the circulation. Further, angiotensin receptor blockers (ARB's) but not ACE inhibitors have been shown to attenuate IH after vascular injury. It is therefore contemplated that elevated chymase levels could underlie the therapeutic advantage of ARB's versus ACE inhibitors in this setting.

Antibodies

Within certain embodiments, the disclosure contemplates antibodies with an epitope to a polypeptide of PSKFCGG (SEQ ID NO: 1) or EIVTSNGPSKFCGG (SEQ ID NO: 2). The disclosure should not be construed as being limited solely to one type of antibody. The antibodies can be produced by immunizing an animal such as, but not limited to, a horse, rabbit, guinea pig, hamster, rat, or a mouse, with a protein, or a portion thereof, or by immunizing an animal using a protein comprising at least a portion of the corresponding polypeptide. One skilled in the art would appreciate, based upon the disclosure provided herein, smaller fragments of these proteins can also be used to produce antibodies that specifically bind the polypeptide. Antibody production may be enhanced by the addition of an adjuvant including, but not limited to, alum. The antibodies may be conjugated to a marker, such as a fluorescent dye or protein, e.g., green fluorescent protein. Sections of the antibodies may be detected by secondary antibodies containing markers.

Certain embodiments of the disclosure encompass polyclonal, monoclonal, synthetic antibodies, and the like. Moreover, the antibody can be used to detect and or measure the amount of protein present in a biological sample using well-known methods such as, but not limited to, Western blotting, radio immunoassay (RIA), and enzyme-linked immunosorbent assay (ELISA). The antibody can also be used to immunoprecipitate and/or immuno-affinity purify their cognate antigen using methods well-known in the art.

It is also contemplated the antibodies may be contained in a pharmaceutical composition for uses that any chymase inhibitor could be used for, such as being administered to a subject for the treatment or prevention of thickening of the walls of arteries or vessels, renal disease, heart disease, or heart attack. Thus, by administering the antibody to a cell or to the tissue of an animal, or to the animal itself, the activity of chymase would therefore be inhibited.

In another embodiment, a monoclonal antibody is obtained from the non-human animal, and then modified, e.g., humanized, deimmunized, chimeric, or produced using recombinant DNA techniques known in the art. A variety of approaches for making chimeric antibodies have been described. See, e.g., U.S. Pat. No. 4,816,567 and U.S. Pat. No. 4,816,397. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a specific target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An antibody or fragment thereof may also be modified by specific deletion of human T cell epitopes or "deimmunization" by the methods disclosed in U.S. Pat. No. 7,125,689 and U.S. Pat. No. 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes and thus constitute potential T cell epitopes. Potential T-cell epitopes detected can be eliminated by substituting small numbers of amino acid residues in the variable domains or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

EXPERIMENTAL

CKD Subjects

Stage 4 and 5 CKD patients were identified between Jul. 14, 2008 and Jul. 31, 2010 who had no prior AV access creation (including central venous catheters), were six or more months from initiating hemodialysis, and were suitable candidates for AVF based on upper extremity venous mapping at the Emory Dialysis Access Center of Atlanta, Emory University Hospital and Emory Midtown Hospital. Subjects were enrolled as part of a study to evaluate the cardiovascular effects of AVF creation. A baseline visit occurred prior to AVF creation, at which time a blood sample, echocardiogram, and six-minute walk test were obtained. Additionally, demographic data, clinical history and medication use were obtained via direct patient interview. Study subjects underwent AVF creation within two days-3 weeks following the baseline visit. The Institutional Review Board (IRB) of Emory University Medical Center approved the study protocol and informed consent was obtained from each patient prior to study enrollment.

ESRD Subjects

Adult ESRD patients receiving outpatient hemodialysis at Emory University dialysis units between Mar. 24, 2009 and Jun. 25, 2010 were identified who were suitable candidates for AVF creation based on upper extremity venous mapping at the Emory Dialysis Access Center of Atlanta, Emory University Hospital and Emory Midtown Hospital. Subjects were enrolled as part of a pilot study to evaluate the impact of vitamin D on AVF maturation, and all subjects included in this analysis were using a central venous catheter at the time of study enrollment. The average time on dialysis was 11.7 months ($\pm$19.8 months). A baseline visit occurred prior to AVF creation, and demographic and clinical data were collected via direct patient interview, at which time a blood sample was obtained. Study subjects underwent AVF creation within 1-3 weeks following the baseline visit. The Institutional Review Board (IRB) of Emory University Medical Center approved the study protocol and informed consent was obtained from each patient prior to study enrollment.

Tissue Collection

Remnants of surgically excised cephalic and basilic veins were collected from 11 CKD and 12 ESRD subjects at the time of AVF creation at Emory University and Emory Midtown Hospitals between Jul. 15, 2008-Jul. 30, 2010, by four vascular surgeons.

A peripheral vein from a non-CKD patient was used as control. Remnant vein segments, which are normally discarded, were harvested from the cephalic or basilic vein to be used as the AVF conduit by the surgeon. It was not possible to obtain vein segments from all study patients because of the limited length of the vessel in some cases. The vein remnants were carefully placed directly into 10% normal buffered formalin without use of forceps. The specimens were transferred to 70% ethanol 24 h after initial placement in formalin. Within 1 week, venous segments were processed and embedded in paraffin blocks. Hematoxylin and eosin stain (H and E) was used to show cellularity and general morphological characteristics.

Tissue Immunohistochemistry

Paraffin-embedded vein segments were sectioned into 3.0-μm-thick serial sections. After heat-mediated antigen retrieval, slides were immunohistochemically processed in a DAKO Automated Immunostainer (DAKO Corp.) using a labeled streptavidin-biotin method for IL-6 (rabbit polycolonal antibody to IL-6 manufactured by Abcam) and TGF-β1 (rabbit polyclonal IgG to TGF-β1 manufactured by Santa Cruz). After processing, slides were coverslipped with a Leica CV5000 Coverslipper (Leica Microsystems, Inc.). Each staining batch contained positive and negative slides; normal colon tissue was the positive control tissue for IL-6, and normal tonsil tissue was the positive control for TGF-β. The negative and positive control slides were treated identically to the patients' slides except that antibody diluents were used rather than primary antibody on the negative slides.

Tissue Immunofluorescence and Confocal Laser Scanning Microscopy

Human veins were immersion-fixed in 4% paraformaldehyde and stored in 70% ethanol until paraffin embedding and sectioning. Sections (5 μm) were mounted on slides, deparaffinized in xylene and rehydrated in ethanol. Sections were blocked with 5% goat serum in 1×PBS for 1 h at room temperature. Primary antibodies (final concentration): ACE rabbit monoclonal (Sigma, 1:250); Chymase (our custom synthesized antibody using services of affinity bioreagents, 1:750) were combined in an appropriate volume of 5% goat serum in 1×PBS, and applied to sections by overnight incubation at 4° C. The sections were incubated with ALEXA® FLOUR® 488 or ALEXA® FLOUR® 647 goat anti-rabbit, to visualize the specific stains. All secondary antibodies were from Molecular Probes. 4' 6-diamidino-2-phenylindole (DAPI) (Vector) was used to visualize nuclear DNA. Image Acquisition was performed on a Zeiss LSM510 META confocal laser scanning microscope (Zeiss, Thornwood, N.Y.) with a LSM510 system cooled CCD camera and software Zeiss ZEN 2008 (Zeiss, Thornwood, N.Y.). In showing chymase staining (micrographs in FIG. 1), chymase was pseudocolored in green and α-SMA in red. In micrographs 2 and 3, chymase was pseudocolored in pink and ACE rendered in green.

Plasma Chymase ELISA Assay

Plasma from normal, CKD and ESRD subjects were diluted in 50 mM of sodium carbonate buffer, pH 9.6 (Sigma, St. Louis, Mo., USA) and plated in COSTAR® 96 well flat bottom Medical-grade polystyrene plates (Corning Life Sciences, Massachusetts, USA) overnight at 4° C. The next day, the samples were washed in PBS containing 1% bovine serum albumin (BSA) and 0.05% TWEEN® 20 (Sigma) and blocked for 2 h with PBS containing 3% goat serum (Sigma) at 37° C. After three washes with PBS containing 1% BSA and 0.05% TWEEN® 20, primary polyclonal antibody specific for chymase (our custom synthesized antibody using services of Affinity Bioreagents) was diluted 1:1000 in PBS containing 3% goat serum and applied to the plate followed by a 37° C. incubation for 1 h. After three washes with PBS containing 1% BSA and 0.05% TWEEN® 20, bound antibody was detected with a secondary horseradish peroxidase (HRP)-conjugated antibody (Sigma) and incubated for 1 h at 37° C. The plate was washed three times with PBS containing 1% BSA and 0.05% TWEEN® 20 and developed with Ultra TMB (PIERCE® Biotechnology, IL, USA). The reaction was stopped using 2 M sulfuric acid (Sigma), and its OD was read at 490 nm by the microplate reader (ELX® 808; Bio-Tek instruments). Standard curve for chymase was prepared by measuring optical absorption from known concentrations.

Human Chymase amino acid 40-53 custom peptide sequence: EIVTSNGPSKFCGG (SEQ ID NO: 2) was used to create antibodies for human chymase after antibody peptide sequence: MAYLEIVTSNGPSKF (SEQ ID NO: 3) failed to produce antibodies that were useful for the detection assay. In the successful EIVTSNGPSKFCGG (SEQ ID NO: 2), PSKF is unique for human chymase.

Clinical data for 29 CKD and 13 ESRD subjects were available for the analysis. Venous tissue was available for analysis on 11 CKD subjects and 12 ESRD subjects. Overall, the average patient age was 58 years, 67% of patients were Black and 67% male. Mean SBP was 140, 93% had hypertension, 43% had diabetes, 59% had a history of tobacco use, and 17% had a history of myocardial infarction (MI) (Table 1). CKD patients were older, less likely to be Black, with lower systolic and diastolic blood pressure compared with ESRD patients. There was no difference between patient cohorts in gender, BMI, prevalence of hypertension, diabetes, smoking history, or history of MI.

TABLE 1

Clinical Characteristics of Study Subjects

| Characteristics | Control (n = 5) | CKD (n = 29) | ESRD (n = 13) | p-value* |
|---|---|---|---|---|
| Age | 26 ± 12.9 | 61.2 ± 12.2 | 51.4 ± 7.9 | 0.004 |
| Black | 0 (0) | 15 (51.7) | 13 (100) | 0.002 |
| Female | 2 (40.0) | 11 (37.9) | 3 (23.1) | 0.485 |
| BMI | 22.6 ± 2.3 | 31.1 ± 8.2 | 29.6 ± 6.1 | 0.508 |
| SBP | 113 ± 6.0 | 135 ± 18.8 | 154 ± 27.8 | 0.042 |
| DBP | 71 ± 7.3 | 72 ± 11.9 | 86 ± 18 | 0.025 |
| Hypertension | 0 (0) | 28 (96.6) | 11 (84.6) | 0.222 |
| Diabetes | 0 (0) | 12 (41.4) | 6 (46.2) | 1 |
| Smoking | 0 (0) | 17 (58.6) | 8 (61.5) | 1 |
| History of MI | 0 (0) | 4 (13.8) | 3 (23.1) | 0.657 |

Results are % or standard deviation.
*p-value compares CKD vs. ESRD patients

Pre-existing IH varied. 10 of 11 (91%) CKD vein segments exhibited IH and luminal stenosis prior to surgical AVF creation, demonstrating that IH exists in CKD patients prior to AVF creation, and cannot be attributed solely to the effects of flow and pressure alterations resulting from AVF creation. 9 of 12 (75%) ESRD vein segments had IH. Abundant chymase was present in vessels with IH, and was diffuse, within the intima and adventitia, and co-localizing in the vessel media with α-smooth muscle actin (α-SMA), reflecting myofibroblast formation (FIG. 1). The same finding was observed in vein samples from ESRD subjects. By contrast, the non-CKD control subject lacked IH, with little evidence of mast cell chymase and no evidence of α-SMA within the vein sample.

Figure 2:
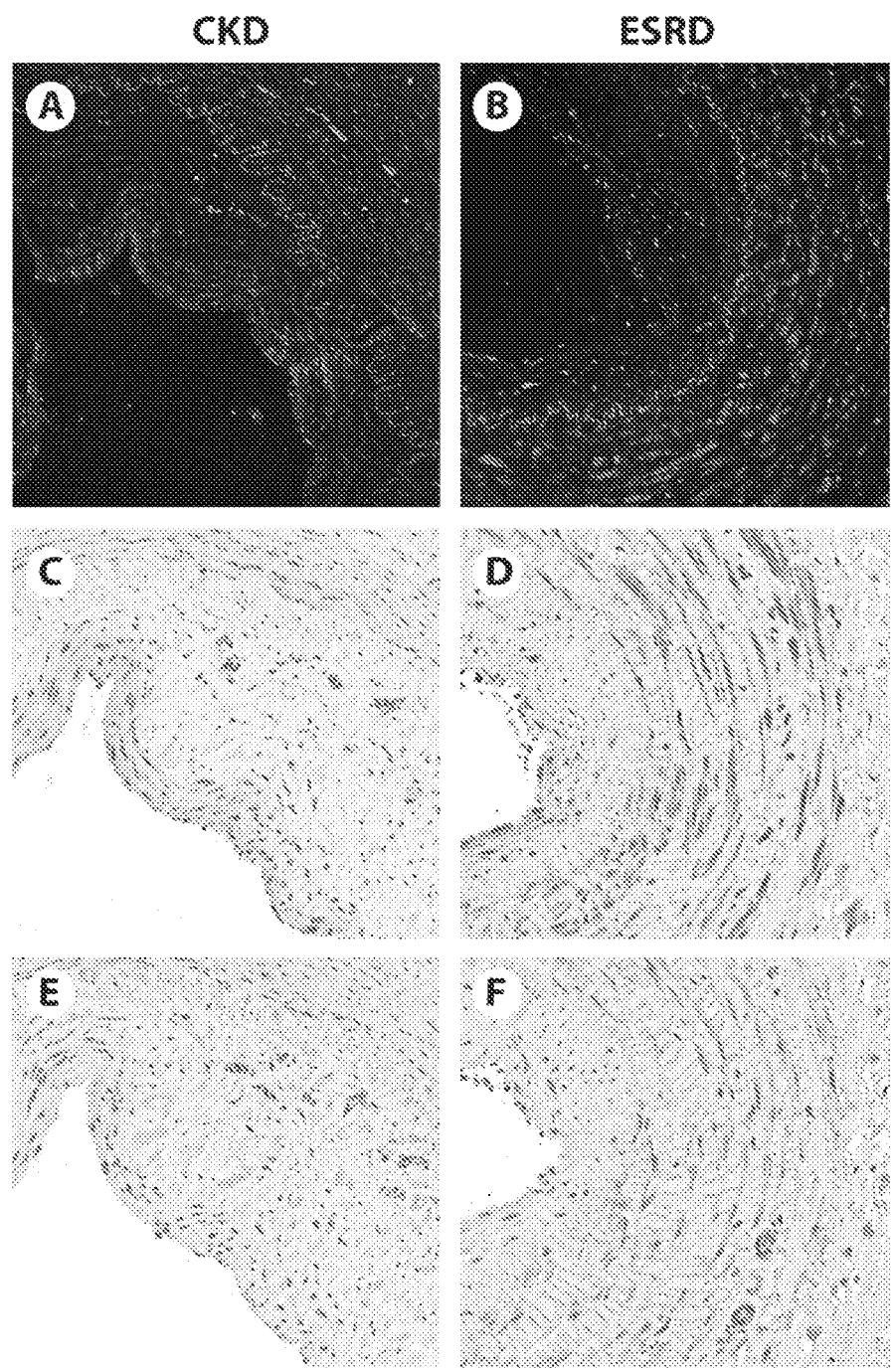
FIG. 2: Serial vein segments from the cephalic vein of a pre-dialysis CKD (a,c,e) and an ESRD (b,d,f) patient. Immunofluorescence (a,b) shows abundant chymase (pink) expression in the thickened vessel intima and media (separated by elastic lamina, blue) of both the CKD and ESRD patient. Immunohistochemistry shows localization of TGF-β (c,d) (brown) and IL-6 (e,f) (brown) primarily within the intima and media, in a similar distribution as chymase.

The distribution of vascular chymase was then compared with two factors which induce IH and are associated with AVF stenosis: transforming growth factor-β (TGF-β) and interleukin-6 (IL-6) (FIG. 2). TGF-β expression was greater in vessels with IH compared to those without IH and was found to be greater in vessel intima and media layers, indicating that TGF-β production is greater in diseased vessels with IH. Veins with IH expressed more IL-6, which was more pronounced in the venous intimal and medial layers. The intensity of TGF-β and IL-6 expression was similar in CKD and ESRD veins with IH.

Figure 3:
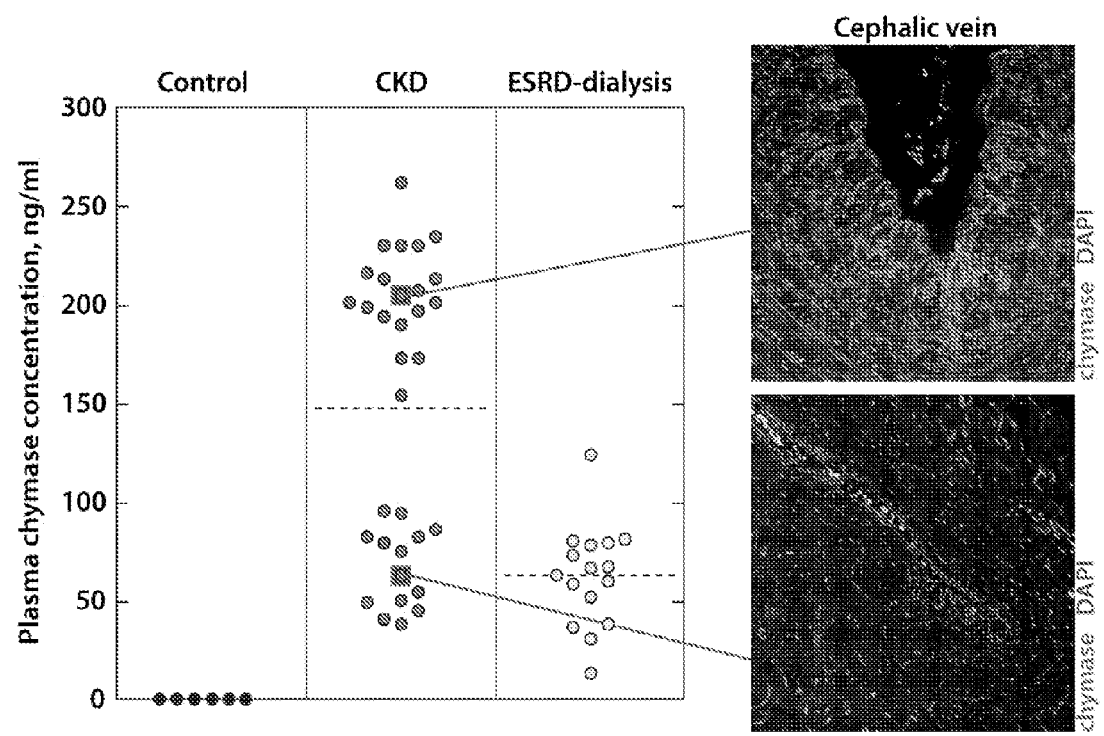
FIG. 3: Plasma chymase concentration by patient cohort. Note bimodal distribution of plasma chymase in CKD patients. Elevated plasma chymase is shown with corresponding mast cell chymase expression in veins of same patients with IH. ESRD patients have a different plasma chymase concentration, suggesting that creatinine clearance may influence plasma chymase.

After finding abundant mast cell chymase in the veins of CKD and ESRD subjects preparing for AVF creation, the relationship between mast cell chymase and plasma chymase concentrations was examined (FIG. 3). The non-CKD control subjects had undetectable plasma chymase concentrations (<8 ng/ml), which corresponded with the virtual lack of mast cell chymase. CKD subjects demonstrated a bimodal distribution of plasma chymase, with plasma chymase concentrations that were as much as 6-fold greater than the lowest group, and abundant mast cell chymase expression. Finally, ESRD subjects had a different plasma chymase distribution than CKD subjects, suggesting that reduced creatinine clearance may be responsible for elevated plasma chymase levels in CKD subjects. Dialysis had an effect on plasma chymase levels, however, it is unlikely that this was due to direct removal of chymase from the bloodstream by dialysis, because chymase exists as a 200 kDA complex with alpha-2 macroglobulin in plasma. This led us to speculate that plasma markers of systemic inflammation may be elevated among CKD patients with the greatest plasma chymase concentrations. However, no association between plasma c-reactive protein and plasma chymase concentrations was found (data not shown). Moreover, the plasma chymase bi-modal distribution was not associated with statin use. Interleukin-6 (IL-6), a local marker of inflammation, was present in vascular IH lesions which express high levels of chymase (FIG. 2).

In a group of CKD patients (n=25) in whom AVF suitability for dialysis within 6 months of AVF creation was determined clinically (ability to cannulate the AVF with 2 needles with dialysis blood flow >300 ml/min for at least 6 dialysis sessions in one month and within 6 months of AVF creation), plasma chymase concentration was examined as a predictor of AVF outcomes. The risk of experiencing AVF nonmaturation for patients with plasma chymase >210 ng/ml is 10.3 times the risk of experiencing AVF nonmaturation for patients with chymase <210 ng/ml. (Table 2). Notably, the bimodal distribution (FIG. 3) suggests that 150 ng/ml may provide the cutpoint for predicting AVF maturation, but this preliminary data suggests otherwise.

TABLE 2

Odds of AVF nonmaturation by chymase concentration

| Outcome Variable | Dichotomized Chymase | | | Continuous |
|---|---|---|---|---|
| | Estimated odds ratio (CI)* | Relative Risk** (CI) | p-value*** | Chymase p-value**** |
| AVF mature (0 = no, referent) | >=150 vs <150 (referent) | | | 0.124 |
| | 0.263 | 3.14 | 0.341 | |
| | (0.0046, 3.308) | (0.407, 24.3) | | |
| | >=210 vs <210 (referent) | | | |
| | 0.0534 | 10.3 | 0.012 | |
| | (0.00086, 0.753) | (1.38, 76.8) | | |
| | >=215 vs <215 (referent) | | | |
| | 0.0204 | 16 | 0.002 | |
| | (0.00026, 0.379) | (2.25, 113.6) | | |

What is claimed is:
1. A method comprising:
   a) assaying a sample for a plasma chymase level, wherein the sample is obtained from a subject diagnosed with chronic kidney disease; and
   b) correlating an elevated level of plasma chymase with a likelihood of developing arteriovenous fistula nonmaturation, wherein the elevated level of plasma chymase is greater than 210 ng/mL, wherein the assaying comprises measuring the plasma chymase level with an anti-chymase antibody, and wherein the anti-chymase antibody binds an epitope comprising PSKFCGG (SEQ ID NO:1).

2. The method of claim 1, further comprising the step of c) reporting the plasma chymase level to the subject or a medical professional or representative thereof.

3. An anti-chymase antibody that binds to an epitope comprising PSKFCGG (SEQ ID NO:1).

\* \* \* \* \*